(12) United States Patent
Norris et al.

(10) Patent No.: US 6,397,092 B1
(45) Date of Patent: May 28, 2002

(54) OVERSAMPLING PULSE OXIMETER

(75) Inventors: Mark A. Norris; D. Alan Hanna, both of Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/465,742

(22) Filed: Dec. 17, 1999

(51) Int. Cl.$^7$ ................................................ A61B 5/00
(52) U.S. Cl. ........................ 600/323; 600/322; 600/336
(58) Field of Search ................................ 600/309–310, 600/316, 322–324, 326, 330, 331, 336; 356/39–41; 375/316, 340, 267, 324, 346, 348, 347, 367

(56) References Cited

U.S. PATENT DOCUMENTS

| | | | |
|---|---|---|---|
| 4,266,544 A | 5/1981 | Hamaguri | |
| 4,759,369 A | 7/1988 | Taylor | |
| 4,800,885 A | 1/1989 | Johnson | |
| 4,819,752 A | 4/1989 | Zelin | |
| 4,846,183 A | 7/1989 | Martin | |
| 5,078,136 A | 1/1992 | Stone et al. | |
| 5,190,038 A | 3/1993 | Polson et al. | |
| 5,285,784 A | 2/1994 | Seeker | |
| 5,348,004 A | 9/1994 | Hollub | |
| 5,492,118 A * | 2/1996 | Gratton et al. | 600/316 |
| 5,638,816 A * | 6/1997 | Kiani-Azarbayjany et al. | 600/316 |
| 5,676,141 A | 10/1997 | Hollub | |
| 5,692,505 A | 12/1997 | Fouts | |
| 5,720,284 A | 2/1998 | Aoyagi et al. | |
| 5,766,125 A | 6/1998 | Aoyagi et al. | 600/310 |
| 5,774,213 A | 6/1998 | Trebino et al. | 356/320 |
| 5,795,292 A | 8/1998 | Lewis et al. | 600/323 |
| 5,800,348 A | 9/1998 | Kaestle | 600/322 |
| 5,803,910 A | 9/1998 | Potratz | 600/330 |
| 5,820,550 A | 10/1998 | Polson et al. | 600/323 |
| 5,846,190 A | 12/1998 | Woehrle | 600/330 |
| 5,860,919 A | 1/1999 | Kiani-Azarbayjany et al. | 600/322 |
| 5,891,024 A | 4/1999 | Jarman et al. | 600/32 |
| 5,919,134 A | 7/1999 | Diab | 600/323 |
| 6,229,856 B1 * | 5/2001 | Diab et al. | 375/316 |

* cited by examiner

Primary Examiner—Kevin Shaver
Assistant Examiner—Matthew Kremer
(74) Attorney, Agent, or Firm—Marsh, Fischmann & Breyfogle LLP

(57) ABSTRACT

An oversampling pulse oximeter includes an analog to digital converter with a sampling rate sufficient to take multiple samples per source cycle. In one embodiment, a pulse oximeter (100) includes two mor more light sources (102) driven by light source drives (104) in response to drive signals from a digital signal processing unit (116). The source drives (104) may drive the sources (102) to produce a frequency division multiplex signal. The optical signals transmitted by the light sources (102) are transmitted through a patient's appendage (103) and impinge on a detector (106). The detector (106) provides an analog current signal representative of the received optical signals. An amplifier circuit (110) converts the analog current signal to an analog voltage signal in addition to performing a number of other functions. The amplifier circuit (110) outputs an analog voltage signal which is representative of the optical signals from the sources (102). This analog voltage signal is received by a fast A/D converter (112) which samples the analog voltage signal to generate a digital voltage signal which can be processed by the digital signal processing unit (116). The fast A/D converter (112) operates at a rate sufficient to take multiple samples per source cycle and may have a sampling frequency, for example, of over 41 kHz. The digital signal processing unit (116) implements software for averaging the samples over a source cycle for improved measurement consistency, improved signal to noise ratio and reduced A/D converter word length.

32 Claims, 4 Drawing Sheets

OVERSAMPLING PULSE OXIMETER

FIELD OF THE INVENTION

The present invention relates in general to pulse oximetry and, in particular, to a pulse oximeter capable of taking multiple digital samples per source cycle and allowing for processing of digital signals for improved consistency and an improved signal to noise ratio.

BACKGROUND OF THE INVENTION

Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of a patient pulse cycle, information can be obtained regarding blood oxygen saturation.

Conventional pulse oximeters generally employ time-division multiplexed (TDM) signals. As noted above, the processing of the electrical signals involves separate consideration of the portions of the signal attributable to each of the sources. Such processing generally also involves consideration of a dark current present when neither source is in an "on" state. In TDM oximeters, the sources are pulsed at different times separated by dark periods. Because the first source "on" period, second source "on" period and dark periods occur at separate times, the associated signal portions can be easily separated for processing.

The algorithms for determining blood oxygen saturation related values are normally implemented in a digital processing unit. Accordingly, one or more analog to digital (A/D) converters are generally interposed between the detector and the digital processing unit. Conventionally, the A/D converter is operative to integrate a signal over a source cycle or dark period and to generate a digital value proportional to the integrated signal. It will be appreciated that this digital value represents an aggregated quantity and does not provide information regarding a signal value at any point on a signal waveform or the shape of the signal waveform within integration periods. The resulting digital signal or signals can be correlated to corresponding intensity values by the digital processing unit, and well known algorithms can then be utilized to obtain the desired blood oxygen saturation values.

SUMMARY OF THE INVENTION

It has been recognized that TDM pulse oximeters with integrating A/D converters as described above have a number of limitations. First, integrating A/D converters do not provide a digital signal that reflects the shape of the analog detector signal. Ideally, the detector signal portion corresponding to a single source would be a square wave having a high value corresponding to source "on" periods and a low value corresponding to "off" periods. In reality, the noted detector signal portion generally includes a ramp up phase associated with source powering up and a ramp down phase associated with an intensity drop off associated with powering down. The characteristics of the resulting signal vary from source to source or over the operating life of a particular source. Integrating A/D converters generally accumulate charge or otherwise integrate over a sampling period to provide an aggregated value per signal cycle. Such a value provides, at best, cumulative information over the sampling period and does not yield information regarding the signal shape within a source cycle. Accordingly, processing options are limited and substantially no signal phase information is provided within a source cycle.

TDM signals also entail certain system architecture and processing limitations. In many cases TDM signals are demultiplexed using hardware filters or other hardware demultiplexers to form separate signal channels. Each of the channels then has its own hardware signal processing components such as amplifiers, A/D converters and the like. This separate processing introduces potential sources of error such as channel dependent gains and increases the size, complexity and expense of the hardware design. Processor based demodulation of TDM signals simplifies system hardware architecture, but the system speed and accuracy may be limited, particularly in implementations involving more than two light sources.

The present invention is directed to an oversampling pulse oximeter where the analog electronic signal is instantaneously sampled at one or more times per source cycle so as to enable tracking of the signal shape. The invention thereby allows for more accurate analysis of the detector output, allows for reduced noise processing options, allows for reduction in the number of bits in the A/D converter word length and allows for identification of phase characteristics within a signal cycle as may be desired for enhanced digital processing. The invention also provides an architecture that supports signal multiplexing other than TDM, and supports more than two light channels with reduced additional hardware. Such an architecture reduces potential sources of error associated with separate hardware for processing each channel and reduces the complexity and size of the hardware design.

According to one aspect of the present invention, an oversampling pulse oximeter is provided. The oximeter generally includes at least first and second sources for emitting light having first and second spectral contents, respectively. For example, the sources may include a red LED and an infrared LED. The pulse oximeter further includes a drive system for pulsing each of the sources such that the sources output first and second optical signals, respectively, wherein each of the signals includes a series of high output periods separated by low output periods. The high output periods generally correspond to an "on" period of the LED and the low output periods correspond to an "off" state of the LED. It will be appreciated that the LEDs may output substantial photonic energy even during the "off" periods. In addition, the intensity of the LED may vary substantially within an "on" period. The pulse oximeter further includes: a detector for receiving the optical signals and providing a detector signal having a detector signal waveform representative of the optical signals; a digital sampler for receiving the detector signals and providing a digital output based on the detector signal, and a processor for using the digital signal to perform processing steps related to determining an oxygen saturation related value. The oxygen saturation related value may be a calculated blood oxygen saturation, a value of an oxygen related analyte, or other value related to an oxygen content of the patient's blood. In accordance with the present invention, the digital sampler is operative for providing a digital value corresponding to a value of the detector signal corresponding to a portion of the detector signal waveform having a time component that is substantially shorter than a cycle of the sources. Preferably, the time component of the detector signal waveform portion measured by the digital sampler is no more than about 10%, and more preferably no more than about 5% of a cycle period of one of the sources. In addition, the digital sampler is preferably operative for providing multiple digital values corresponding to a single high output period and/or a single low output period of one of the first and second sources.

The digital sampler preferably samples the detector signal at a sufficient rate to accurately track the shape of the detector signal and eliminate or otherwise account for potential sources of measurement error. In this regard, the sampler preferably takes at least about three digital values corresponding to a single high output period of one of the first and second sources. More preferably, the digital sampler has a sampling rate sufficient to obtain at least about 10 and even more preferably at least about 20 digital values corresponding to a single high output period of one of the first and second sources. Such a sampling rate allows for accurate detection of a signal phase of interest and also provides for processing involving data averaging which increases the signal to noise ratio of the digital signal under analysis. Such averaging also increases the dynamic range of the system for a given A/D converter word length, allowing use of the converter of a lower word length. In addition, such a high sampling rate can allow for identification of measurements contaminated by electromagnetic radiation by taking a sufficient number of measurements to recognize incorrect variation in the detected signal. Such averaging also improves consistency of the measurements provided by the pulse oximeter.

Optionally, a fast A/D converter may be used in accordance with the present invention to detect a phase of interest of a detector signal. The associated apparatus comprises: an analog to digital converter, operatively disposed between oximeter detector circuitry and a processing unit, for receiving at least a portion of an analog electrical signal from the detector circuitry and converting the received analog electrical signal portion into a digital signal; a phase detector for analyzing the digital signal to detect a phase of interest relative to the digital signal; and processing logic for processing the digital signal based on the detected phase of interest. For example, the detected phase of interest may be used to identify a subset of digital values from the A/D converter corresponding to a center band portion of an "on" period of one of the sources or other phase of interest. In this manner, variations associated with signal ramping can be accounted for. In addition, the phase detector may be used to synchronize a demodulation function to a modulating signal for a light source, and to trigger a buffering time period to ensure buffering of values corresponding to an integer number of "on" periods for a light channel.

BRIEF DESCRIPTION OF THE DRAWINGS

For a more complete understanding of the present invention and further advantages thereof, reference is now made to the following detailed description taken in conjunction with the drawings, in which.

DETAILED DESCRIPTION OF THE INVENTION

In the following description, the invention is set forth in the context of a two channel, frequency division multiplexed pulse oximeter with an oversampling A/D converter. It will be appreciated however that various aspects of the present invention are applicable in connection with alternative pulse oximeter implementations. For example, the present invention can be used in connection with TDM or other non-TDM multiplexed signals. In addition, the present invention accommodates pulse oximeters with more than two channels. Moreover, although the invention is disclosed in connection with a preferred hardware implementation where all of the light channels are processed by common hardware components and various signal processing functions are implemented in digital processing, the light channels may be processed in separate hardware channels and additional analog processing components may be utilized while taking advantage of certain teachings of the present invention. Accordingly, the following description should be understood as exemplifying the invention, and the scope of the invention is not limited to any such specific implementations.

Figure 1:
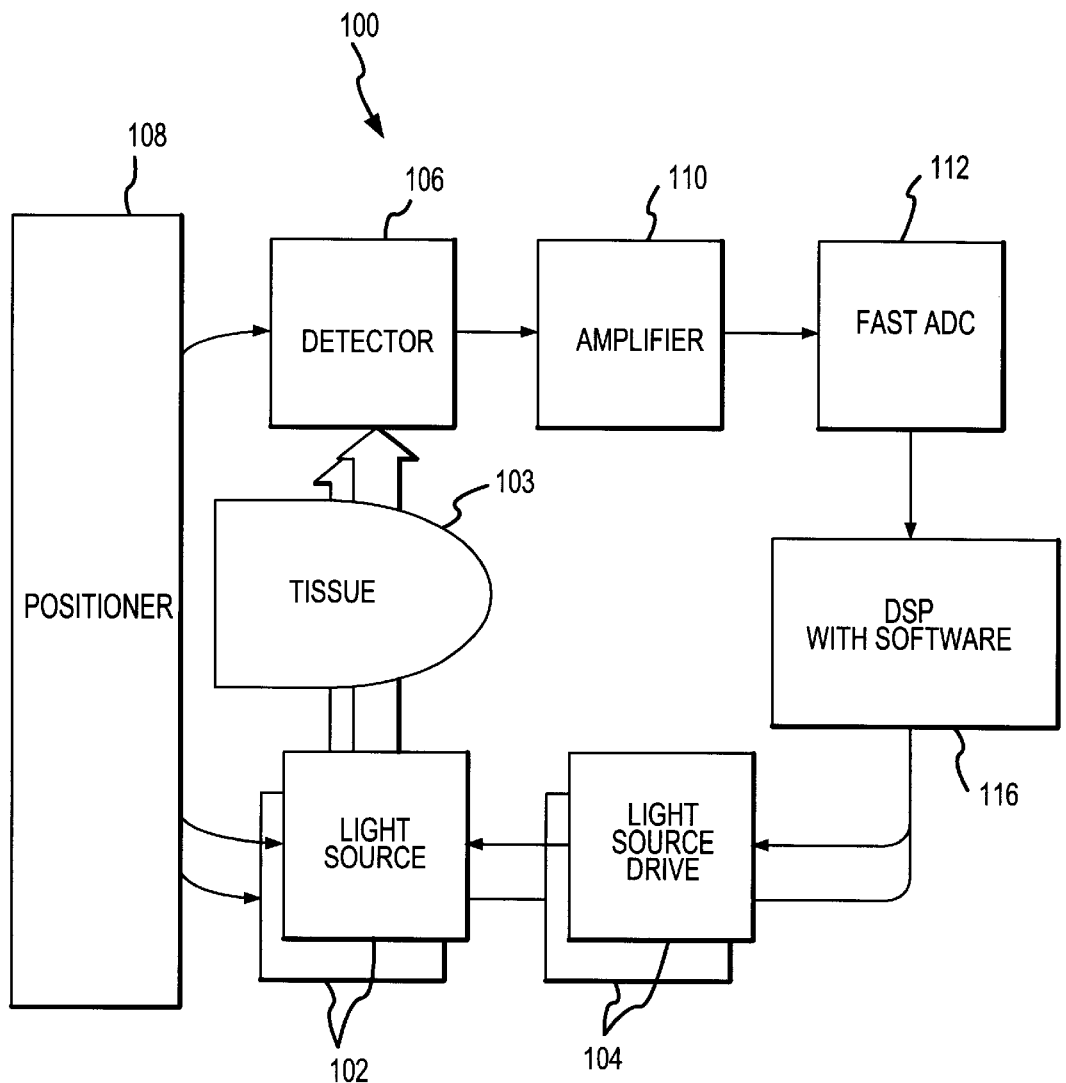
FIG. 1 is a schematic diagram of a pulse oximeter in accordance with the present invention.

Referring to FIG. 1, a pulse oximeter in accordance with the present invention is generally identified by the reference numeral 100. The pulse oximeter 100 includes two or more light sources 102 for transmitting optical signals through, or transmitting optical signals to be reflected from, an appendage 103 of a patient. In the illustrated embodiment, two light sources 102 are shown. For example, the light sources 102 may include a red LED and an infrared LED. The light sources 102 are driven by light source drives 104 in response to drive signals from a digital signal processing unit 116. As discussed above, various multiplexing systems may be utilized in accordance with the present invention. Such multiplexing mechanisms include time division multiplexing, frequency division multiplexing and other non-time division multiplexing systems. In the illustrated embodiment, as will be described in more detail below, the signals from the light sources 102 are modulated using different frequency modulated signals. For example, the source drive 104 associated with the red light source 102 may pulse the red light source at a first frequency and the light source drive 104 associated with the infra-red light source 102 may pulse the infrared light source 102 at a second frequency different from the first frequency. It will be appreciated that such a multiplexing system does not necessarily result in a composite time division multiplexed signal. That is, during certain time periods, both the red source 102 and the infrared source 102 may both be in an "on" state. It should also be noted that although the following description references "on" and "off" cycles for each of the sources 102, in reality, the optical signals associated with each source 102 do not define an ideal square wave. Rather, substantial photonic energy is emitted even in the "off" state. In addition, the intensity transmitted by each of the sources 102 can vary substantially within an "on" cycle. The ability to recognize and address such non-ideal characteristics is an important advantage of the present invention.

The optical signals transmitted by the light sources 102 in the illustrated embodiment are transmitted through the patient's appendage 103 and impinge upon a detector 106. In this regard, a positioner 108 provides for proper alignment of the sources 102 and the detector 106. Various different types of positioners 108 are available depending, for example, on the appendage to be irradiated and on the patient (e.g. different positioners 108 may be provided for neonatal and adult patients). One typical type of positioner 108 is provided in the form of a clothespin-like clamp which engages a patient's fingertip. When the positioner 108 is engaged on the patient's fingertip, the light sources are positioned on one side of the patient's finger and the detector 106 is positioned on the opposite side in alignment with the light sources so as to receive the optical signals transmitted through the patient's finger. It will be appreciated that, in alternative implementations, a reflective pulse oximeter may be employed whereby the sources and detector are located on the same side of the patient's appendage so as to receive optical signals reflected back from the patient's tissue.

The detector 106 receives the optical signals transmitted through the patient's appendage 103 and provides an analog signal representative of the received optical signals. In the illustrated embodiment, the detector 106 outputs an analog current signal where the magnitude of the current at any given time is proportional to the intensity of the received optical signal. The detector signal in the illustrated embodiment is then processed by an amplifier circuit 110. The amplifier circuit may serve a number of functions. First, the illustrated amplifier circuit is operative for converting the input analog current signal from the detector 106 into an analog voltage signal. The amplifier circuit 110 may also be operative for subtracting certain DC and low frequency components from the detector signal. For example, one DC component which may be subtracted from the detector signal relates to photonic energy transmitted by the sources 102 during "dark periods." That is, as noted above, practical source implementations generally transmit a signal of some intensity even during off periods. In addition, low frequency ambient light may be subtracted from the detector signal. The amplifier circuit 110 may also filter out certain high frequency electronic noise and provide other signal processing functionality.

The amplifier circuit 110 outputs an analog voltage signal which is representative of the optical signals (or frequency division multiplexed signal) from the sources 102. This analog voltage signal is received by a fast A/D converter 112 which samples the analog voltage signal to generate a digital voltage signal which can be processed by the digital signal processing unit 116. An important aspect of the present invention relates to the manner in which the input analog voltage signal is sampled by the fast A/D converter 112. In particular, in accordance with the present invention, the converter 112 takes multiple digital samples per cycle of each of the sources 102. That is, the sampling rate of the converter 112 is sufficiently fast to take one or more samples and, more preferably at least about 3 samples and, even more preferably at least about 20 samples per "on" period of each of the sources 102. As will be described in more detail below, such multiple sampling per cycle allows the oximeter to track the shape of the detector signal, to allow for reduced noise processing of the resulting digital signal, to reduce the required A/D converter word length and to identify phase components of interest within a signal cycle. In one implementation, one of the sources 102 is pulsed at a modulating frequency of about 578 Hz. The other source 102 is pulsed at a modulating frequency of about 867 Hz. The frequency modulated composite signal is sampled by the converter 112 at a frequency of about 41,667 Hz. Based on the above noted modulating frequencies as well as the duty cycle of the sources, the converter 112 will sample about 24 times for the shortest "on" cycle. Multiple samples per dark period are also obtained. It will thus be appreciated that the values output by the converter 112 are not integrated or aggregate values corresponding to a source cycle period or dark period, but rather, are substantially instantaneous values reflecting the detector signal at a moment within a cycle. Accordingly, even a single value per cycle provides information regarding the waveform that is not available from an integrated value, and multiple values provide additional processing advantages as described below.

Figure 2:
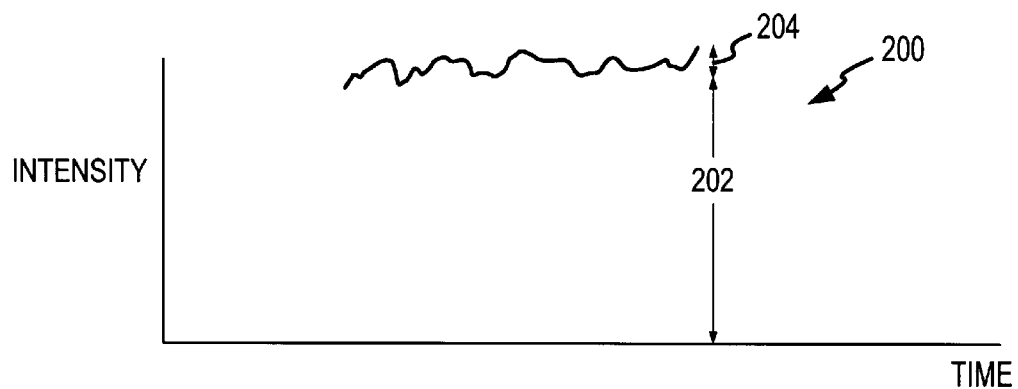
FIG. 2 depicts an analog signal output by the detector of the pulse oximeter of FIG. 1.
Figure 3:
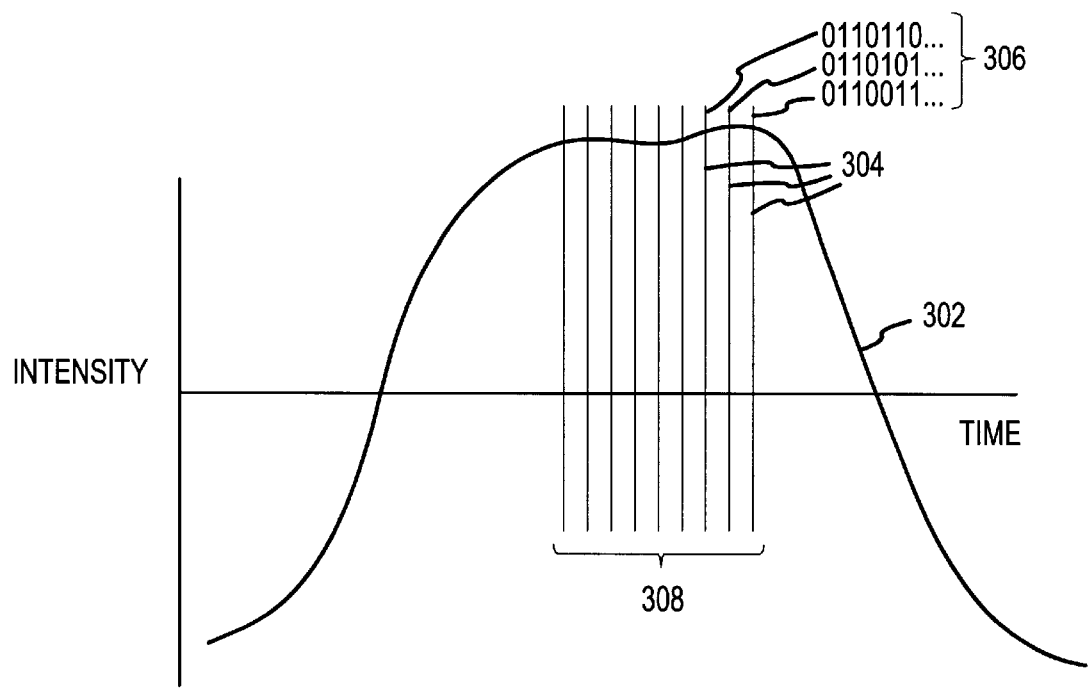
FIG. 3 is a graphic illustration of a digital sampling process in accordance with the present invention.

Such signal processing may be better understood by reference to FIGS. 2–3. FIG. 2 illustrates the signal 200 output by the DSP 116 after demodulation. As shown, the signal includes a relatively small AC component 204 on top of a much larger DC component 202. The primary composition of the DC component 202 is different from the DC and low frequency ambient components discussed above. In particular, a principal portion of the DC component 202 is due to non-pulsatile absorption characteristics of the patient's appendage 103. Accordingly, in order to accurately measure the AC component 204 from which oxygen saturation calculations can be made, the converter 112 preferably provides a high degree of resolution. As discussed in more detail below, certain processing techniques enabled by the oversampling converter 112 provide for improved dynamic range so as to facilitate direct digital conversion of the input analog signal without circuitry for separating the DC and AC components while using an A/D converter with a shorter word length than would otherwise be required.

FIG. 3 illustrates the digital sampling process implemented by the converter 112. In particular, FIG. 3 illustrates a signal portion 302 corresponding to a single "on" cycle of one of the sources 102. It will be appreciated that, in the frequency division multiplexed system as illustrated, the "on" periods of the various sources 102 may overlap. However, for purposes of illustration, the illustrated signal portion 302 is shown as corresponding to an "on" period of one source 102 without interference from or superimposition of a signal component due to the other source 102. As shown, the signal portion 302 is sampled at many time periods 304 within the illustrated cycle. For each sampling period, the converter 112 outputs a digital value, for example, a 16-bit digital stream. These time correlated digital values cumulatively define a digital signal 306 which is transmitted to the digital signal processing unit 116.

Figure 5:
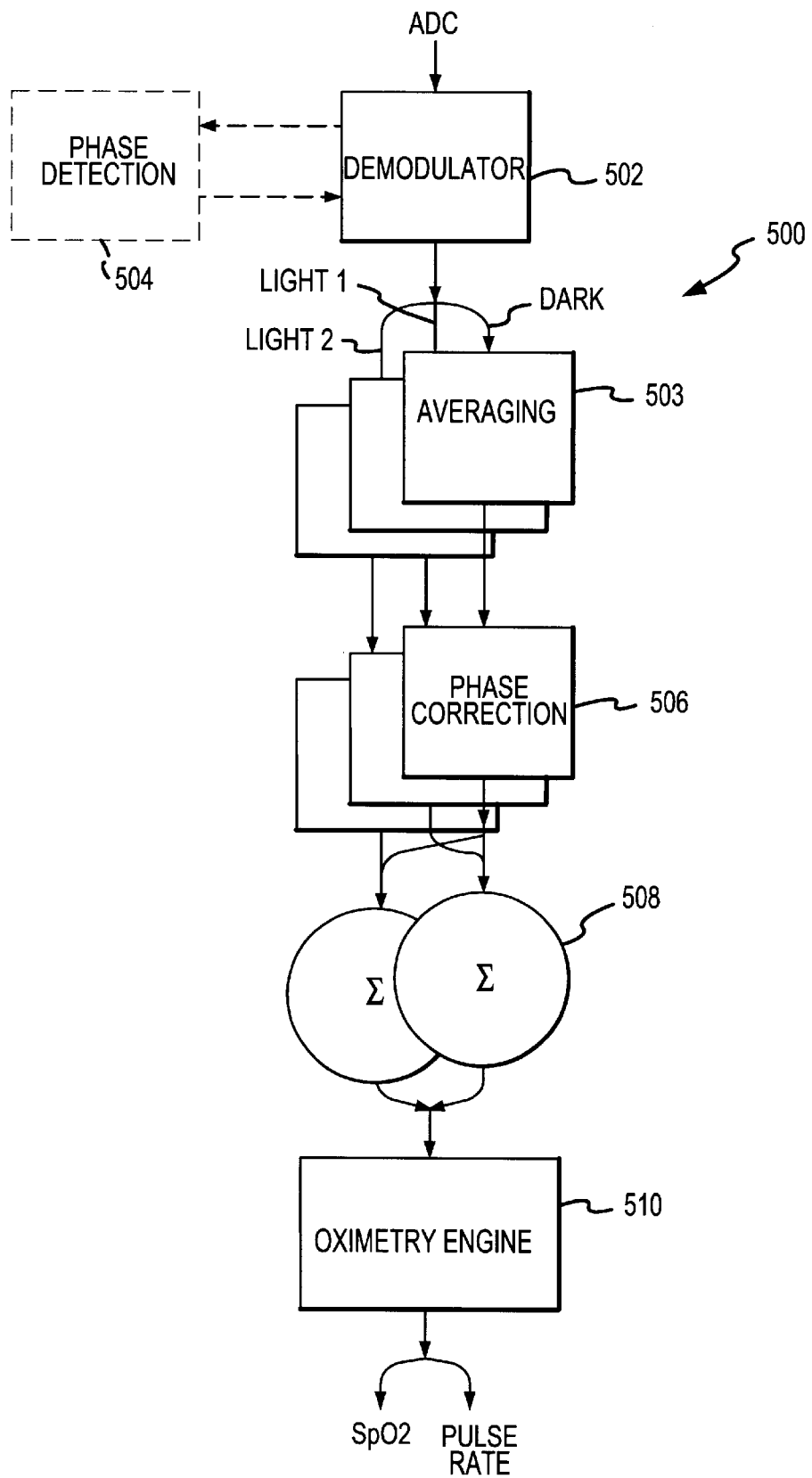
FIG. 5 illustrates various software modules implemented in the digital signal processor of the pulse oximeter of FIG. 1.

The digital signal is transmitted to the digital signal processing unit 116 which implements a number of software modules as generally illustrated in FIG. 5. Referring to FIG. 5, the first illustrated software module is the demodulator 502. In accordance with the present invention, the digital signal received from the A/D converter is a composite signal including portions due to each of the two or more sources. This implementation of the invention is advantageous because it eliminates potential sources of error associated with separate hardware processing channels. However, the oxygen saturation calculations implemented in the illustrated digital processing unit involve analysis of the portions of the digital signal due to each of the light sources. Accordingly, the demodulator 502 is operative for processing the input digital signal so as to yield two separate signals (or sets of values) that are proportional to the contributions of each of the sources. This is accomplished by processing the input digital signal with a demodulation function for each of the light sources. Because the light sources are modulated in the illustrated embodiment using different modulation frequencies, corresponding demodulation functions can be selected to derive from the composite digital signal values that are proportional to the contribution of each of the light sources.

The illustrated software of modules 500 optionally include a phase detection module 503 (shown on phantom). As noted above, the fast A/D converter allows for tracking of the shape of the detector signal. In this regard, it may be useful to identify a particular phase of the detector signal for use in processing. For example, as noted above, practical LED designs do not output a perfect square waveform but rather include a ramping portion associated with powering up of the LED and a ramp down portion associated with diode turnoff. Accordingly, the waveform associated with a particular "on" period can vary from diode to diode or over the life of a diode. It may therefore be desirable to process a subset of values corresponding to only a portion of an "on" period so as to avoid sampling the variable ramping portions of the signal cycle. It will be appreciated that this can be accomplished by directly synchronizing sampling with the source drive signals. Alternatively, as may be desired for certain applications, the shape of the waveform can be monitored to identify a phase characteristic that can be used to synchronize the sampling with the desired portion of the wave cycle. For example, the high output and low output portions of a signal cycle may correlate to a logical plus one and minus one respectively. The phase detection module may identify a time when the logical value passes through zero and use this phase to select a portion of the digital signal to be used in subsequent blood oxygen level calculations. Alternatively, the digital signal may be analyzed to identify a phase associated with a maximum value and this phase may be utilized to select a subset of the digital signal values for use in subsequent processing.

Figure 4:
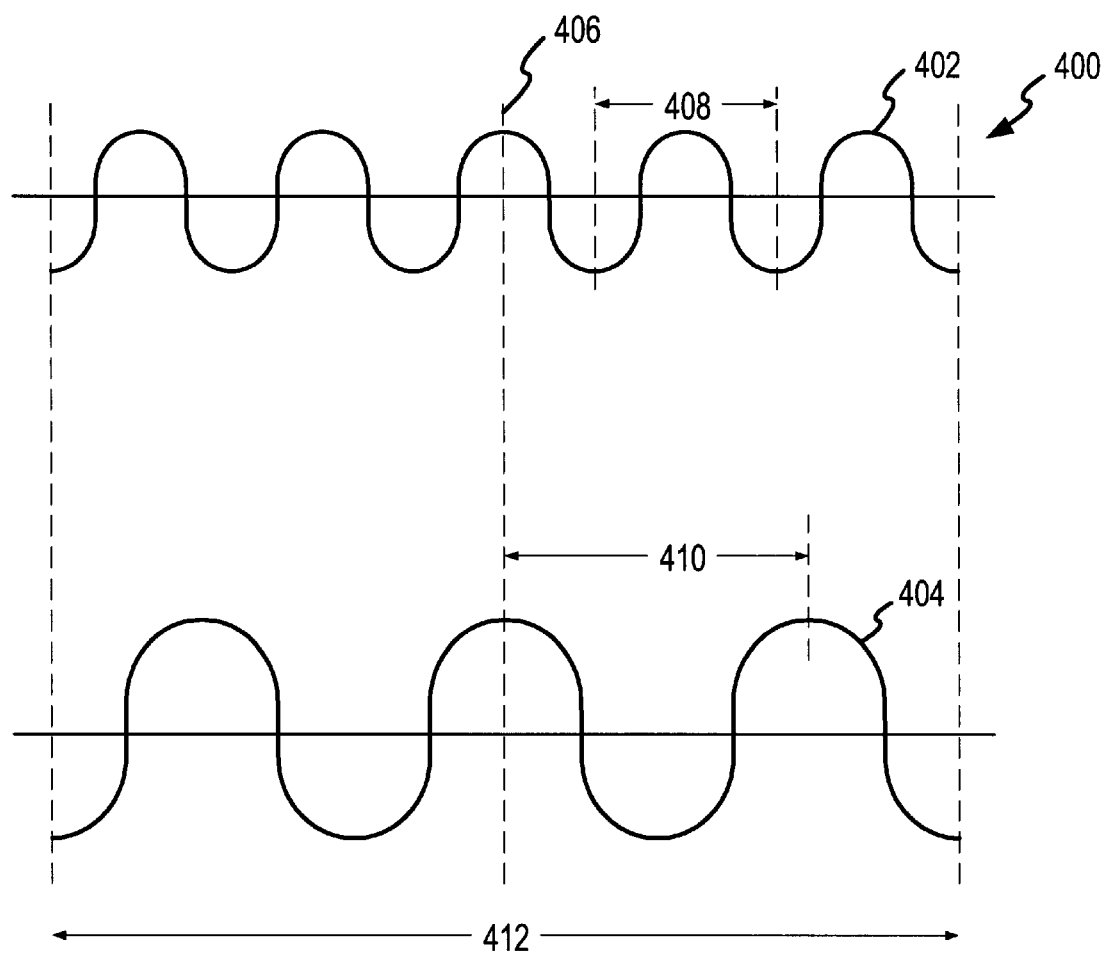
FIG. 4 illustrates the frequency modulated optical signals from the sources of the pulse oximeter of FIG. 1.

FIG. 4 illustrates another possible use of the optional phase detection module 503. In particular, FIG. 4 illustrates modulated signals 400 from each of the light sources. As shown, the first signal 402 associated with one of the sources is modulated at a higher frequency than the frequency 404 associated with the other source. Stated differently, a wavelength 408 of the first signal 402 is shorter than a wavelength 410 of the second signal 404. In order to facilitate processing, it is useful to accurately synchronize the demodulation functions used for each of the light channels to the corresponding modulation signal. In addition, as illustrated in FIG. 4, it is useful in this regard to synchronize the modulating signals to one another. In the illustrated embodiment, it will be observed that within the time period 412, each of the signals 402 and 404 is symmetrical about a center line 406. Moreover, within the period 412 each of the signals includes an integer number of "on" cycles. The latter characteristic is useful for implementations involving buffering multiple samples and using a regression analysis such as a linear regression analysis in order to perform oxygen saturation calculations. It will be appreciated that, with regard to both synchronizing the demodulation signals and selecting the buffering time period, it is useful to synchronize the associated processing relative to the signal phase. Again, such synchronization can be directly implemented by reference to the source drive signal. Alternatively, the optional phase detector 503 can be used in this regard to insure proper processing.

The software modules 500 also include averaging modules 504 for operating on each of the demodulated light channels as well as on a dark channel (associated with a time period where neither of the sources is on). Once the digital signal processing unit has acquired a sample, it places the sample in a queue associated with the corresponding light or dark channel. The digital signal processing unit is then operative to subtract "dark time" samples from samples gathered during a sample interval. The averaging module 504 then reduces the sample rate through a series of steps. First, to ensure that such decimation does not add noise to the reduced sample rate system, a filter attenuates frequencies that decimation aliases back into the final passband while leaving the passband unattenuated. In the illustrated embodiment, the associated filter attenuate such frequencies by more than 127 dB. It will be appreciated that this filter is a software based filter that filters a digital signal by multiplying samples by appropriate coefficients and summing the result. Linear low pass filters meeting these requirements can be readily generated and implemented.

Specifically, in the illustrated embodiment, the filter stage attenuates all frequencies between 10 Hz and 20 kHz by 160 dB. Such a filter requires roughly 100 coefficients. Then the averaging unit 503 decimates the queue by 20 times. Filtering is performed at the end of every other interval, producing about one new data value 250 times per second. These data values are placed into a 250 Hz sample queue for that light channel. Every fifth sample, the sampling module 504 runs the data through a 40 Hz low pass filter and decimates to 50 samples per second. Every other 50 Hz sample, the module 503 low pass filters to 15 Hz and outputs the data 25 times per second. This last stage of filtering takes about 30 coefficients due to the steep transition band of 10 Hz to 15 Hz.

The noted oversampling with summation and decimation down to the sampling frequency results in an increase in the signal to noise ratio proportional to the square root of the oversampling ratio. The dynamic range of the process is also increased in the same proportion. For example, if the converter samples at twice the sampling rate used during signal processing, the signal strength doubles but more noise also enters the data stream. In effect, a 2×oversampling rate doubles the noise. However, uncorrelated Gaussian RMS noise adds as the square root of the sum of the squares. Accordingly, the signal strength doubles while the noise increases by the square root of 2. Thus, the signal to noise ratio is increased by the square root of 2. Accordingly, decimation and summing results in a 10 dB increase in signal to noise ratio per decade of oversampling. The above noted filtering process also results in an improvement in the signal to noise ratio. Also, the required A/D converter word length is reduced by 1 bit for each doubling of the signal to noise ratio.

In the pulse oximeter 100 of FIG. 1, the digital signal processing obtains a roughly 127 dB signal to noise ratio. The converter 112 provides about a 100 dB signal to noise ratio at 50,000 samples per second. The passband is 10 Hz wide for an oversampling ratio of 500 times. Using 10 dB per decade of oversampling, oversampling adds 27 dB to the signal to noise ratio. This compares favorably with signal to noise ratios in analog signal processing pulse oximeters.

The software modules 500 also include a phase correction module 506. This phase correction module may be used in TDM implementations so as to mathematically adjust readings associated with sequential "on" periods of the separate sources to adjust for the time difference so that, mathematically, the samples are taken at the same time. Similar phase correction functionality may be utilized in connection with non-TDM systems. The phase corrected signals are then processed by summing software 508. As shown, the summing software combines a reading from each light channel with a dark current reading. In this manner, the dark current reading can be subtracted from the signal corresponding to each light channel in order to eliminate effects due to ambient noise and other dark current components. The resulting values are then fed to an oximetry engine 510 which implements conventional algorithms in order to determine an oxygen saturation value and, if desired, a pulse rate for the patient.

Although the present invention has been described in several embodiments, various changes and modifications may be suggested to one skilled in the art. It is intended that the present invention encompass such changes and modifications that fall within the scope of the appended claims.

What is claimed is:

1. A pulse oximeter, comprising:
    a first source for emitting light having a first spectral content;
    a second source for emitting light having a second spectral content different than said first spectral content;
    a drive system for pulsing each of said first and second sources such that said first and second sources output first and second optical signals, respectively, each of said first and second optical signals including a series of high output periods separated by low output periods, said drive system thereby defining a modulation waveform;
    a detector for receiving said first and second optical signals and providing a detector signal representative of said received first and second optical signals; and
    a digital sampler, operatively associated with said detector, for providing multiple digital values based on said detector signal corresponding to a single cycle state, said single cycle state being one of a single high output period and a single low output period of one of said first and second sources; and
    a processor for using said multiple digital values in performing processing steps related to determining an oxygen saturation related value, said processing steps including processing said multiple digital values to obtain modulation waveform information relating to a shape of said modulation waveform, said shape including a profile of a portion of said detector signal corresponding to said single cycle state, and using said modulation waveform information in determining said oxygen saturation related value.

2. A pulse oximeter as set forth in claim 1, wherein said first source emits red light and said second source emits infrared light.

3. A pulse oximeter as set forth in claim 1, wherein said drive system pulses each of said first and second light sources so that said first and second optical signals define a composite time division multiplexed signal, wherein the respective high output periods of the first and second optical signals are substantially free from temporal overlap.

4. A pulse oximeter as set forth in claim 1, wherein said drive system pulses said first light source based on a first modulating signal and pulses said second light source based on a second modulating signal so that the first and second optical signals define a composite signal including temporal overlap events where the respective high output periods of the first and second optical signals temporally overlap.

5. A pulse oximeter as set forth in claim 1, wherein said detector signal provided by said detector is an analog current signal reflecting an intensity of light incident on said detector as a function of time.

6. A pulse oximeter as set forth in claim 5, further comprising circuitry for receiving said analog current signal and outputting an analog voltage signal representative of said first and second optical signals.

7. A pulse oximeter as set forth in claim 6, wherein said circuitry is further operative for subtracting one of a DC component and a low frequency component from said analog current signal such that said subtracted component is not reflected in said analog voltage signal.

8. A pulse oximeter as set forth in claim 1, wherein said digital sampler has a sampling rate sufficient to obtain at least about 3 of said digital values corresponding to said single cycle state.

9. A pulse oximeter as set forth in claim 1, wherein said digital sampler has a sampling rate sufficient to obtain at least about 20 of said digital values corresponding to said single cycle state.

10. A pulse oximeter as set forth in claim 1, wherein said digital sampler outputs a digital signal to said processor including a first portion representative of said first optical signal and a second portion representative of said second optical signal, and said processor implements demodulation logic for extracting from said digital signal a first set of data corresponding to said first portion of said digital signal and a second set of data corresponding to said second portion of said digital signal.

11. A pulse oximeter as set forth in claim 1, wherein said processor implements averaging logic for receiving multiple values corresponding to a single high output period of one of said first and second sources and for determining an intensity related value based on said multiple values.

12. A pulse oximeter as set forth in claim 1, wherein said processor is operative for processing said digital values of said digital sampler to identify a phase of interest relative to said detector signal, and said processor includes selection logic for selecting a subset of said digital values based on said identified phase, wherein said selected subset is used in determining said oxygen saturation related value.

13. A pulse oximeter as set forth in claim 1, wherein said processor is operative for processing said digital values of said digital sampler to identify a phase of interest relative to said detector signal, and said processor includes demodulation logic for extracting, from a digital signal received from said digital sampler, a portion of said digital signal corresponding to a contribution to said digital signal from one of said sources, said demodulation logic employing a demodulation function, wherein said demodulation function is synchronized relative to said digital signal based on said identified phase.

14. A pulse oximeter as set forth in claim 1, further comprising means for correcting a phase related to a time difference between measurements first and second high output periods of said first and second sources, respectively.

15. A pulse oximeter, comprising:
    a first source for emitting light having a first spectral content;
    a second source for emitting light having a second spectral content different than said first spectral content;
    a drive system for pulsing each of said first and second sources such that said first and second sources output first and second modulated optical signals, respectively, each of said first and second optical signals including a series of high output periods separated by low output periods;
    a detector for receiving said first and second optical signals and providing a detector signal having a detector signal waveform representative of said received first and second optical signals; and
    a digital sampler, operatively associated with said detector, for providing a series of digital values, each said digital value corresponding to a value of said detector signal relating to a portion of said detector signal waveform having a time component that is substantially shorter than any of said high output periods of said sources, whereby said series of values includes multiple values corresponding to each one of said high output periods, said series of values defining a digital signal;

a processor for performing processing steps related to determining an oxygen saturation related value;

a demodulator, operatively interposed between said digital sampler and said processor, for receiving a first input signal based on said detector signal and demodulating said input signal based on a modulating pattern of said drive system, said input signal including multiple values corresponding to each one of said high output periods; and a multi-stage decimation unit, operatively interposed between said digital sampler and said processor, for receiving a second input signal based on said detector signal and performing a first decimation process on said second input signal to provide a first decimated signal having a first compressed sample set relative to said second input signal and performing a second decimation process on said first decimated signal to provide a second decimated signal having a second compressed sample set relative to said first decimated signal.

16. A pulse oximeter as set forth in claim 15, wherein said time component of said portion of said detector signal waveform is no more than about 50% of one of said high output periods.

17. A pulse oximeter as set forth in claim 15, wherein said time component of said portion of said detector signal waveform is no more than about 10% of one of said high output periods.

18. A pulse oximeter as set forth in claim 15, wherein said drive system pulses each of said first and second light sources so that said first and second optical signals define a composite time division multiplexed signal, wherein the respective high output periods of the first and second optical signals are substantially free from temporal overlap.

19. A pulse oximeter as set forth in claim 15 wherein said drive system pulses said first light source based on a first modulating signal and pulses said second light source based on a second modulating signal so that the first and second optical signals define a composite signal including temporal overlap events where the respective high output periods of the first and second optical signals temporally overlap.

20. A pulse oximeter as set forth in claim 15, wherein said digital sampler has a sampling rate that is sufficiently fast to track a shape of said detector signal, said shape including a profile of a portion of said detector signal corresponding to a single high output period of one of said first and second sources.

21. An apparatus for use in a pulse oximeter that includes a first source for emitting light at a first wavelength, a second source for emitting light at a second wavelength, a drive system for pulsing each of said sources so as to define an optical signal including a series of "on" periods for each of the sources, detector circuitry for receiving the optical signal and providing an analog electrical signal representative thereof, and a saturation calculation unit for determining oxygen saturation values based on the electrical signal, said apparatus comprising:

receiving means for receiving at least a portion of said analog electrical signal;

an analog to digital converter for converting said received analog electrical signal portion into a digital signal, said analog to digital converter being operative for sampling said analog electrical signal portion at a sampling rate and providing corresponding digital values;

said sampling rate being sufficient to provide multiple digital values corresponding to a single "on" period of one of said sources; and a processor for using said multiple digital values in performing processing steps including processing said multiple digital values to obtain modulation waveform information relating to a shape of said modulation waveform, said shape including a profile of a portion of said detector signal corresponding to said single "on" period, and using said modulation waveform information in processing said digital signal.

22. A pulse oximeter as set forth in claim 20, wherein said drive system pulses each of said first and second sources so that said optical signal is a composite time division multiplexed signal, wherein respective high output periods of the first and second sources are substantially free from temporal overlap.

23. A pulse oximeter as set forth in claim 20 wherein said drive system pulses said first source based on a first modulating signal and pulses said second source based on a second modulating signal so that the optical signal is a composite signal including temporal overlap events where the respective high output periods of the first and second optical signals temporally overlap.

24. A pulse oximeter as set forth in claim 20, wherein said analog to digital converter has a sampling rate sufficient to obtain at least about 3 of said digital values corresponding to a single high output period of one of said first and second sources.

25. A pulse oximeter as set forth in claim 20, wherein said analog to digital converted has sampling rate sufficient to obtain at least about 20 of said digital values corresponding to a single high output period of one of said first and second sources.

26. An apparatus for use in a pulse oximeter that includes a first source for emitting light at a first wavelength, a second source for emitting light at a second wavelength, a drive system for pulsing each of said sources so as to define an optical signal including a series of "on" periods for each of the sources, detector circuitry for receiving the optical signal and providing an analog electrical signal representative thereof, and a saturation calculation unit for determining oxygen saturation values based on the electrical signal, said apparatus comprising:

an analog to digital converter, operatively disposed between said detector circuitry and said processing unit, for receiving at least a portion of said analog electrical signal and converting said received analog electrical signal portion into a digital signal;

a phase detector for analyzing the digital signal to detect a phase of interest relative to said digital signal;

processing logic for processing said digital signal based on said detected phase of interest;

a demodulator, operatively interposed between said analog to digital converter and said saturation calculation unit for receiving a first input signal based on said electrical signal and demodulating said input signal based on a modulating pattern of said drive system, said input signal including multiple values corresponding to each one of said "on" periods; and a multi-stage decimation unit, operatively interposed between said analog to digital converter and said saturation calculation unit, for receiving a second input signal based on said electrical signal and performing a first decimation process on said second input signal to provide a first decimated signal having a first compressed sample set relative to said second input signal and performing a second decimation process on said first decimated signal to provide a second decimated signal having a second compressed sample set relative to said first decimated signal.

27. A pulse oximeter as set forth in claim 26, wherein said drive system pulses each of said first and second light sources so that said first and second optical signals define a composite time division multiplexed signal, wherein the respective "on" periods of the first and second optical signals are substantially free from temporal overlap.

28. A pulse oximeter as set forth in claim 26, wherein said drive system pulses said first light source based on a first modulating signal and pulses said second light source based on a second modulating signal so that the first and second optical signals define a composite signal including temporal overlap events where the respective high output periods of the first and second optical signals temporally overlap.

29. A pulse oximeter as set forth in claim 26, wherein said analog to digital converter has a sampling rate sufficient to obtain at least about 3 of said digital values corresponding to an instant of single high output period of one of said first and second sources.

30. A pulse oximeter as set forth in claim 26, wherein said analog to digital converter has a sampling rate sufficient to obtain at least about 20 digital values corresponding to a single "on" period of one of said first and second sources.

31. A pulse oximeter as set forth in claim 26, wherein said processing logic includes selection logic for selecting a subset of digital values based on said identified phase, wherein said selected subset is used in determining said oxygen saturation related values.

32. A pulse oximeter as set forth in claim 26 wherein said demodulator is operative for extracting, from said first input signal, a portion of said first input signal corresponding to a contribution to said first input signal from one of said sources, said demodulation logic employing a demodulation function, wherein said demodulator function is synchronized relative to said first input signal based on said identified phase.

* * * * *

UNITED STATES PATENT AND TRADEMARK OFFICE
CERTIFICATE OF CORRECTION

PATENT NO.     : 6,397,092 B1
DATED          : May 28, 2002
INVENTOR(S)    : Norris et al.

It is certified that error appears in the above-identified patent and that said Letters Patent is hereby corrected as shown below:

<u>Column 14,</u>
Line 18, delete the word "demodulator", and insert therefor -- demodulation --.

Signed and Sealed this

Sixteenth Day of July, 2002

*Attest:*

*Attesting Officer*

JAMES E. ROGAN
*Director of the United States Patent and Trademark Office*